United States Patent [19]

Langerbeins et al.

[11] Patent Number: 4,713,483

[45] Date of Patent: Dec. 15, 1987

[54] PROCESS FOR THE PRODUCTION OF OXALIC ACID DIESTERS

[75] Inventors: Klaus Langerbeins, Langen; Günther Schröder, Ober-Ramstadt; Hans-Peter Boehm, Ottobrunn, all of Fed. Rep. of Germany

[73] Assignee: Röhm GmbH Chemische Fabrik, Darmstadt, Fed. Rep. of Germany

[21] Appl. No.: 849,858

[22] Filed: Apr. 9, 1986

[30] Foreign Application Priority Data

Apr. 13, 1985 [DE] Fed. Rep. of Germany ....... 3513255

[51] Int. Cl.$^4$ ............................................. C07C 67/36
[52] U.S. Cl. ..................................... 560/204; 502/181; 502/185; 502/230; 560/193
[58] Field of Search ................. 560/204, 193; 502/230, 502/181, 185

[56] References Cited

U.S. PATENT DOCUMENTS 3,393,136  7/1968  Fenton et al. ........................ 560/204
3,994,960 11/1976  Yamazaki et al. ................... 560/204

FOREIGN PATENT DOCUMENTS 2514685 10/1975  Fed. Rep. of Germany .
2601139  7/1976  Fed. Rep. of Germany .
2721734 12/1977  Fed. Rep. of Germany .
2814708 10/1978  Fed. Rep. of Germany .

Primary Examiner—Werren B. Lone
Assistant Examiner—Vera C. Clarke
Attorney, Agent, or Firm—Oblon, Fisher, Spivak, McClelland & Maier

[57]    ABSTRACT

A process for the production of diesters of oxalic acid by oxidative carbonylation of alcohols with carbon monoxide and oxygen as oxidizer at pressures of 1 to 700 atmospheres and in a temperature range between 20° and 250° C. in a reaction phase containing the alcohol and, as catalyst, palladium and at least one metal halide in catalytically effective amounts, whereby a catalyst system is used which consists of palladium, at least one metal halide, and an activated carbon which has been pretreated before use by heating to 200°–1,500° C. in a gas atmosphere G, differing from air.

The gas atmosphere G, differing from air, consists, preferably, of at least one of the gases (a) nitrogen; (b) nitrogen compounds, except those with nitrogen-oxygen bonds; or (c) carbon monoxide; and may optionally contain an accompanying gas.

23 Claims, No Drawings

PROCESS FOR THE PRODUCTION OF OXALIC ACID DIESTERS

BACKGROUND OF THE INVENTION

1. Field of the Invention

The invention concerns a procedure for the production of oxalic acid diesters by the oxidative carbonylization of alcohols with the use of palladium catalysts.

2. Background of the Invention

The production of oxalic acid esters from the apropriate alcohols by means of oxidative carbonylation through the catalytic effect of a metal from the platinum group has been described many times.

From U.S. Pat. No. 3,393,136 a procedure for the production of saturated oxalic acid esters is known, in which an essentially water-free reaction medium, consisting of a saturated simple $C_1$–$C_{12}$ alcohol and 0.001 to 2% by weight of a metal from the platinum group as well as 0.05 to 5% by weight of a redox salt from the group of soluble Cu(II) and iron (III) salts, is brought into contact with carbon monoxide and oxygen simultaneously, in order to retain the redox salt at its highest oxidation level, at temperatures between 30° and 300° C. and pressures between 5 and 700 atmospheres. In DE-OS No. 22 13 435 there is also a suggestion for the production of oxalic acids and their esters in which carbon monoxide in an aqueous or alcoholic phase is oxidized with oxygen under pressure and at an elevated temperature in the presence of a catalytic system composed of a salt or a complex of a platinum metal and a salt or a complex of another metal which is more electropositive than the cited precious metals and which can appear at various oxidation levels. Also required is the conversion of insoluble or difficultly soluble platinum metal salts into soluble complexes by the addition of an alkali salt.

DE-OS No. 25 14 685 describes a procedure for the production of dialkyl oxalates by the conversion of an aliphatic alcohol with carbon monoxide and oxygen under pressure in the presence of a catalyst (consisting of a mixture of a salt, a metal of the platinum group and a salt of copper or iron) and possibly in the presence of an alkali metal salt, whereby the conversion is carried out in the presence of an activator. The group of cited "activators" is—in chemical terms—very inhomogenous. It includes, e.g., inorganic bases such as alkali hydroxides and carbonates as well as neutral substances known for their drying effect, such as, e.g., $Na_2SO_4$ and $MgSO_4$. The effect of nitrates may be related to the participation of nitrites or esters formed in the redox procedures during the oxidative carbonylization [see also European application No. 0 056 993, European application No. 0 056 994, DE-OS No. 27 33 730, European application No. 0 057 629, European application No. 0 057 630, European application No. 0 046 983, Japanese published application No. 83-21646, (Chem. Abstr. 98, 160258a), Japanese published application No. 83-126836 (Chem. Abstr. 99, 194450j), and European published application No. 0 105 480].

From DE-OS No. 26 01 139 a procedure is known which is characterized by the use of added ammonia or amines. A further development is suggested in DE-OS No. 27 21 734, according to which a halide-free ammonium salt is used in addition to amines and the copper (II) compound is also supposed to be free of halide ions.

In U.S. Pat. No. 4,005,128 the use of at least stoichiometric amounts of amines under the exclusion of halides of the catalyst metals is suggested. According to U.S. Pat. No. 4,005,129 and DE-PS No. 27 21 734 this suggestion is supplemented by the addition of halogen-free ammonium salts, e.g. salts of sulfuric, acetic or trifluoroacetic acid. In DE-OS No. 28 14 708 the use of acidic co-catalysts is recommended.

Although the general suitability of precious metal catalysts of the platinum group in conjunction with redox systems such as Cu-II or Fe-III for the catalytic effect on the oxidative carbonylization of alcohols could be deduced from the state of the art, the various proposed variations presented a rather confusing, if not contradictory, picture.

More recently, heterogeneous catalysis with palladium containing mixed catalysts has gained increasing attention. In U.S. Pat. No. 4,447,638, the catalytic effect of a mixed catalyst of Pd or Pd salts in combinaton with crystalline vanadium oxide, phosphorus oides and titanium oxides has been employed. In U.S. Pat. No. 4,451,666 a comparable catalyst system is recommended, in which titanium has been replaced by manganese. According to U.S. Pat. No. 4,447,639, iron instead of titanium or manganese is used in the mixed catalysts. From Japanese published application No. 84,05 143 (Chem. Abstr. 100, 174285v) a procedure is known in which the carbon monoxide and oxygen, together with catalysts that contain tetramine-palladium(II)-nitrate on carbon, is reacted in the autoclave, and in Japanese published application No. 84-05144 (Chem. Abstr. 100, 113511q) a similar catalyst, containing T1 in addition, is recommended. In Japanese published application No. 81-142239 (Chem. Abstr. 96,68378), a process is suggested in which palladium metal has been added to activated carbon and the halogen components are present as the soluble component of the catalyst.

As a rule, in homogenous catalysis a considerable reduction of the catalytic effect is observed during continuous operation. Heterogeneous contact catalysis can provide certain advantages as compared to homogenous catalysis. It is, for example, usually easier to separate the catalyst components. This makes their reuse simpler. In addition, it does not cause precipitation of the heavy metal ions in the solution, the recycling of which into the original catalyst form can be very expensive.

However, even the state-of-the-art procedures which operate with heterogeneous catalysis are not wholly satisfactory. Especially the long reaction times and the yield obtained leave much to be desired.

Thus, there remains the problem of developing heterogeneously working contact catalysts which, with relatively short reaction times, provide a high yield of oxalic acid esters and have a high selectivity in the oxidative carbonylation of alcohols. In addition, the catalyst system should not be less readily accessible and not more costly than the ones already in use.

SUMMARY OF THE INVENTION

Accordingly, it is an object of the invention to provide a heterogeneous catalyst that, with relatively short reaction time, provides a high yield of oxalic acid esters with a high selectivity in the oxidative carbonylization of alcohols. According to the invention, the problem is solved by a procedure for the production of diesters of oxalic acid by oxidative carbonylization of alcohols with carbon monoxide and with oxygen as oxidizing agents under a pressure of from 1 to 700 atmospheres and in the temperature range of 20° to 250° C. in a reaction phase which contains the alcohol and, as catalyst, palladium and at least one metal halide in catalytically effective amounts, whereby a catalyst system of palladium, at least one metal halide and specially pretreated activated carbon AK is used in heterogeneous catalysis. The special pretreatment of the activated carbon consists of a thermal treatment of the activated carbon in a temperature range of 200°-1,500° C., preferably 600°-1,300° C., in a gaseous atmosphere, different from air.

DESCRIPTION OF THE PREFERRED EMBODIMENTS

The gaseous atmosphere, differing from air, preferably consists of one of the gases (a) to (c) listed below:

(a) nitrogen;

(b) nitrogen compounds, except those with nitrogen-oxygen bonds; or (c) carbon monoxide.

The gaseous atmosphere may also contain as an additional component (d) an accompanying gas, which is described later in detail. At times in this specification this gaseous atmosphere is referred to as "gaseous atmosphere G" or by a similar phrase. Nitrogen compounds, except those with nitrogen-oxygen bonds, are preferably selected from the following:

(b1) ammonia and its alkyl derivatives;

(b2) hydrazine and its alkyl derivatives;

(b3) hydrogen cyanide and its derivatives such as dicyanogen and alkyl nitriles;

(b4) unsaturated nitriles such as acrylic and methacrylic nitrile; or (b5) amides and hydrazides of $C_1-C_2$ carbonic acids as well as their N-alkyl derivatives; whereby "alkyl" is to be understood as preferably representing $C_1-C_2$ alkyl, especially methyl. Component (c), carbon monoxide, also includes CO donors, i.e. substances with CO bonds in the molecule that release carbon monoxide under the applied conditions (200°-1,500° C.). For example, formamide, N-alkylformamides (such as methyl formamide, and dimethyl formamide), formaldehyde, and methylal are cited. Also suitable is the use of gas mixtures, e.g. of (a) with (b) and/or (c). It appears to be advantageous to use nitrogen- or carbon-containing gases with a molecular weight of not more than 75, preferably not more than 30. The boiling point of the gases, where they are not already gaseous at room temperature, should be below 200° C. and, as a rule, not exceed 160° C. (at 760 mm). Particularly preferred is a gaseous atmosphere containing ammonia or carbon monoxide or consisting thereof. Understood as accompanying gases (d) are, e.g., air or the gases of which it is composed; however, activation with air (naturally occurring atmosphere containing nitrogen as the exclusively activating gas) is not considered sufficient in the sense of the current invention.

There are no obstacles to the use of accompanying gases (d) in any amount during the activation according to the invention of the activated carbon, as their use is not critical. However, a dilution of the particularly active gases (a)-(c) leads to a tendency towards prolongation of the activation process. As a rule, the accompanying gas (d) is present in lower amounts from 0 to 50% by volume, relative to the gaseous atmosphere, preferably less than 20% by volume.

The heating of the activated carbon (also known as activated charcoal) in a gaseous atmosphere consisting of $H_2O$ and/or $O_2$ also causes an effective activation which, however, does not reach the activation attained by means of the gases (a)-(c). The pretreatment by heating suitably takes between 1 and 120 minutes. Activated carbon is considered—in accordance with standard technical definitions (see Ullmann's Encyclopedia of Technical Chemistry, 4th edition, Vol. 14, p. 620-633, herein incorporated by reference)—to consist of porous carbon structures, usually with interior surface areas between 500 and 1,500 $m^2/g$, determined according to the BET method (DIN 66131, incorporated herein by reference). The use of so-called shaped catalytic carbon is, however, preferred; it is also possible to use granulated (water purification) carbon, as well as powdery carbon used for decolouring. Preferably the activated carbon used has a pore volume around 1.2 ml/g (according to DIN 66131). The content of palladium in the catalyst system suitably is near 0.05 to 1 mole, relative to each 100 ml of the alcohol (in discontinuous operation).

The ratio of activated carbon to palladium used is in the range of 5:1 parts by weight up to 500:1 parts by weight, preferably 10:1 to 100:1 parts by weight.

Thus, the procedure according to the invention serves for the production of diesters of oxalic aid by conversion of CO with alcohols in the presence of oxygen (oxidative carbonylation) at pressures of 1 to 700 atmospheres, preferably with pressures of 1 to 250 atmopheres, and in a temperature range of from 20° and 250° C., preferably in the range of 50° to 150° C., in a reaction phase which contains the alcohol and, as a catalytic system consisting of palladium, also at least one metal halide (i.e. not a palladium compound) in catalytically effective amounts and the activated carbon.

As in the alcohols suitable for the reaction, no critical limitation exists. The alcohols used in the state of the art are suitable for the reaction, e.g. possibly substituted alcohols with 1 to 10 carbon atoms, especially primary and secondary aliphatic, as well as alicyclic and aralkyl alcohols. Especially mentioned should be the alcohols with 1 to 6 carbon atoms.

The procedure is suitable for continuous as well as discontinuous operation. (See Ullmann's Encyclopedia of Technical Chemistry, 4th edition, Vol. 13, pg. 539-569, Publisher Chemie, herein incorporated by reference.) The continuous process will be preferred, especially for commercial production. A particularly advantageous embodiment of the process is using a pressure reactor containing the heterogeneous part of the catalyst and equipped with two circuits, one each for the liquid and for the gaseous components of the reaction mixture.

From the liquid circuit a component is taken out for obtaining the oxalic acid ester. The spent gases, CO and oxygen, are fed into the gaseous circuit. To increase the procedural safety, it is suitable to keep the oxygen concentration below the explosion level. However, to attain the highest possible space-time yield, the "safety gap" to the explosion level should not be selected as too large, as with dropping oxygen concentration the space-time yield will drop as expected. Oxygen can be used in the form of pure oxygen or in the form of air, whereby in general the use of pure oxygen is to be preferred, as with the use of air the nitrogen which is not participating in the reaction would unnecessarily consume compression energy, and the removal of the nitrogen from the reaction product would cause an additional expense.

The Catalyst System

Palladium can be present, preferably in the form of palladium metal. (See Ullmann's Encyclopedia of Technical Chemistry, 4th edition, Vol. 13, pg. 539–569, Verlag Chemie, herein incorporated by reference.) Suitable care should be taken that the palladium is used in a well-distributed form. The palladium can be, e.g., well distributed on the activated carbon; however, the catalytic effect is already apparent when finely distributed elementary palladium and activated carbon are put to use side-by-side. "Pd-Mohr" or "Pd-Black" are to be considered finely distributed palladium. As metal halides, the chlorides, bromides and in particular iodides of the metals from the first main group, as well as of the second main group of the periodic system, are cited in particular. As a rule they are at least partially soluble in the reaction mixture. The metal halides are in a molar ratio to the palladium of 1:200 to 10:1, preferably 1:10 to 1:100. The practical execution of the procedure can be carried out as follows:

The activated carbon: It is to be understood that the thermal pretreatment is certainly not the usual thermal treatment of carbon for the production of activated carbon (see Ullmann, loc. cit.), but a thermal activation, preferably carried out just prior to use, of what is usually commercially available activated carbon. For example, the activated carbon offered by the Merck Company in Darmstadt can be used. The reactors suitable for the activation of the activated carbon can be those used in the field, consisting of sufficiently thermally stable and inert materials, such as glass, ceramics, inert metals as, e.g., V2A ® steel, which can be heated in a controlled manner, in any well-known procedure, for example by means of heating elements mounted on the outside in connection with control devices, such as thermal regulators. The treatment time is suitably in the range of 1–120 minutes, generally about 20–45 minutes, preferably near 30 minutes. Longer treatment times are possible, but as a rule are not necessary. Within the reactors a gas atmosphere G is created, preferably by leading the gas or gases through. The flow of the gases is suitably in the range of 1–50 l/h, preferably 5–20 l/h. Preferred is the use of activated carbon which has been treated as follows: The original activated carbon, e.g., type 2184 MERCK-Aktivkohle, is treated in a glass tube which can be heated from the outside with temperature control, by the transfer of the corresponding gas at the desired temperature. The thus-obtained activated carbon types can be seen from the following Table I.

TABLE I

| Treated activated carbon (AK types) | Type of Gas | Treatment Temperature (°C.) | Treatment time (min.) |
| --- | --- | --- | --- |
| AK I | $NH_3$ | 1,150 | 30 |
| AK II | $N_2$ | 1,150 | 30 |
| AK III | $H_2O$ | 600 | 30 |
| AK IV | Air | 800 | 30 |
| AK V | $(CN)_2/N_2$ | 1,150 | 30 |
| AK VI | CO | 1,100 | 30 |
| AK VII | $NH_3$ | 800 | 120 |

General Description of the batch test in the autoclave (Samples 1–13)

Fifty ml each of the alcohol (see below) and a mixture of palladium (e.g. product from the Janssen Company, Nettetal), the treated activated carbon (e.g. AK I to AK V), and metal halide are filled into a 0.35 liter autoclave with Hastelloy C4 ® insert, electric heat and magnetic stirrer. Then, CO and air are turned on and the autoclave heated.

The catalysts, reaction times and temperatures used, as well as yield and selectivity are summarized in Tables II and III.

The evaluation of the test results is done by gas chromatograph analysis. As the by-products formaldehyde and methyl iodide are produced only at very low concentration, they are not evaluated.

TABLE II

| Sample No. | Alcohol | Catalyst amount (mol) | System Compos. | Reaction pressure (bar) | Cond.[1] time (min.) | Autoclave temp. (°C.) | Oxalate in prod. (wt %) | Ratio oxalate/ carbonate expressed as wt % |
| --- | --- | --- | --- | --- | --- | --- | --- | --- |
| 1 | $CH_3OH$ | 2 | Pd | 140 | 15 | 80 | 15.1 | 82/18 |
|   |          | 4 | NaI |     |    |    |      |       |
|   |          | 167 | AK I* |   |    |    |      |       |
| 2 | $CH_3OH$ | 2 | Pd | 140 | 15 | 80 | 6.9 | 90/10 |
|   |          | 4 | NaI |     |    |    |      |       |
|   |          | 167 | AK II* |  |    |    |      |       |
| 3 | $CH_3OH$ | 2 | Pd | 140 | 15 | 80 | 6.3 | 89/11 |
|   |          | 4 | NaI |     |    |    |      |       |
|   |          | 167 | AK III* | |    |    |      |       |
| 4 | $CH_3OH$ | 2 | Pd | 140 | 15 | 80 | 6.4 | 90/10 |
|   |          | 4 | NaI |     |    |    |      |       |
|   |          | 167 | AK IV* | |    |    |      |       |
| 5 | $CH_3OH$ | 2 | Pd | 140 | 15 | 80 | 11.0 | 92/08 |
|   |          | 4 | NaI |     |    |    |      |       |
|   |          | 167 | AK VI* | |    |    |      |       |
| 6 | $CH_3OH$ | 2 | Pd | 140 | 15 | 80 | 4.2 | 89/11 |
|   |          | 4 | NaI |     |    |    |      |       |
|   |          | 167 | ** |     |    |    |      |       |
| 7 | $CH_3OH$ | 2 | Pd | 140 | 15 | 80 | 10.6 | 76/24 |
|   |          | 4 | NaI |     |    |    |      |       |
|   |          | 167 | AK V* |  |    |    |      |       |
| 8 | $CH_3OH$ | 2 | Pd | 140 | 15 | 80 | 8.9 | 81/19 |
|   |          | 4 | NaI |     |    |    |      |       |
|   |          | 167 | ** |     |    |    |      |       |
| 9 | $CH_3OH$ | 2 | Pd | 140 | 15 | 80 | 5.9 | 86/14 |
|   |          | 4 | NaI |     |    |    |      |       |

TABLE II-continued

| Sample No. | Alcohol | Catalyst amount (mol) | System Compos. | Reaction pressure (bar) | Cond.[1] time (min.) | Autoclave temp. (°C.) | Oxalate in prod. (wt %) | Ratio oxalate/ carbonate expressed as wt % |
|---|---|---|---|---|---|---|---|---|
| 10 | CH$_3$OH | 167<br>2<br>4<br>167 | <br>Pd<br>NaI<br> | 140 | 15 | 80 | 2.5 | 83/17 |
| 11 | CH$_3$OH | 2<br>4<br>167 | Pd<br>NaI<br>** | 140 | 15 | 80 | 3.9[2] | 85/15 |
| 12 | CH$_3$OH | 2<br>4<br>167 | Pd<br>NaI<br>** | 140 | 15 | 80 | 1.1[2] | 85/15 |
| 13 | CH$_3$OH | 2<br>4<br>167 | Pd<br>NaI<br>** | 140 | 15 | 80 | 1.3 | 62/38 |

*Treated activated carbon according to Table I.
**Comparison test with untreated activated carbon.
[1]CO:O$_2$ = 4.1 (O$_2$ as air).
[2]Vol %

TABLE III

| Sample No. | Alcohol | Catalyst amount (mol) | System Compos. | Reaction pressure (bar) | Cond.[3] time (min.) | Autoclave temp. (°C.) | Oxalate in prod. (wt %) | Ratio oxalate/ carbonate expressed as wt % | RZA[5] (g/l.h) |
|---|---|---|---|---|---|---|---|---|---|
| 14 | CH$_3$OH | 4.4<br>0.25[4]<br>2,300 | Pd<br>NaI<br>AK I* | 180 | 15 | 95 | 6.1 | 78/22 | 143 |
| 15 | CH$_3$OH | 4.4<br>0.25<br>2,300 | Pd<br>NaI<br>AK I* | 180 | 15 | 95 | 4.1 | 84/16 | 96 |
| 16 | CH$_3$OH | 4.4<br>0.25[4]<br>2,300 | Pd<br>NaI<br>AK I* | 180 | 15 | 95 | 8.9 | 75/23 | 104 |
| 17 | CH$_3$OH | 4.4<br>0.25[4]<br>2,300 | Pd<br>NaI<br>AK I* | 180 | 15 | 95 | 5.9 | 77/23 | 69 |

*Treated activated carbon according to Table I.
**Comparison test with untreated activated carbon.
[3]CO:O$_2$ = 8:1 (O$_2$ as pure oxygen).
[4]0.25 mmol NaI/100 ml solution.
[5]RZA = Raum-Zeit Ausbeute = Space-time yield.

General Description of the continuous testing (Samples 14–17)

The reaction container consists of an electrically heated tube reactor (volume: 70 ccm, inside diameter: 10 mm), which is filled with a mixture of 10 g palladium on granulated activated carbon (product of the Ventron company, Karlsruhe) and 20 g granulated activated carbon (originating from Merck, Darmstadt) with an average granule size of 2.5 mm. Lead into the reactor from below is methanolic NaI solution (concentration=0.25 mmol/100 ml MeOH) and the mixture of carbon monoxide and pure oxygen (ratio 8:1).

Before entering the reactor, the gas mixture is compressed in a compressor. The pressure in the reaction container is regulated by opening and closing of a chamber valve at the reactor exit. The reactor product—consisting of a gaseous and a liquid phase exits hot and is cooled to about 10°–15° C., and the liquid phase is separated by means of a separator (volume approximately 30 cm$^2$.

Setting the pressure at 15–20 bar in the separator by means of a pin valve at the exit proved to be advantageous in view of an almost complete separation of the partially volatile reaction product.

Advantageous Effects

The process according to the invention is very well suited for solving the problems of the prior art and is distinguished by a high selectivity and suitable space-time yield. For the production of dimethyl oxalate it is possible, for example, to expect a spacetime yield of >96 g/l/hour.

What is claimed as new and desired to be secured by Letters Patent of the U.S. is:

1. The process for the production of a diester of oxalic acid, which comprises oxidatively carbonylating an alcohol with carbon monoxide and oxygen as oxidizers at a pressure of from 1 to 700 atmospheres and at a temperature of from 20° to 250° C. in a reaction phase which contains the said alcohol and a catalyst comprising palladium and at least one metal halide in catalytically effective amounts, together with an activated carbon which is pretreated before use by heating to 200° to 1500° C. in a gas atmosphere that is different from air and which contains at least one of the following gases:
  (a) nitrogen
  (b1) ammonia or an alkyl derivative of ammonia;
  (b2) hydrazine or an alkyl derivative of hydrazine;
  (b3) hydrogen cyanide, dicyanogen or an alkyl nitrile;
  (b4) an unsaturated nitrile;

(b5) an amide or a hydrazide of a $C_1$-$C_2$ carbonic acid or an N-alkyl derivative of an amide or a hydrazide of $C_1$-$C_2$ carbonic acid; or (c) carbon monoxide.

2. The process of claim 1, wherein said gas atmoshphere also contains an accompanying gas other than components (a)–(c).

3. The process of claim 1, wherein said gas atmosphere contains ammonia.

4. The process of claim 1, wherein said gas atmosphere contains carbon monoxide.

5. The process of claim 1, wherein said metal halide comprises an iodide, chloride or bromide of a metal of the first main group of the periodic system.

6. The process of claim 1, wherein said metal halide comprises a bromide or iodide of an alkali metal.

7. The process of claim 1, wherein said activated carbon has been pretreated by heating to 200°–1,500° C. for 1 to 120 minutes.

8. The process of claim 1, wherein said activated carbon has been pretreated by heating to 600°–1,300° C. for 1 to 120 minutes.

9. The process of claim 1, wherein said reaction temperature for the oxidative carbonylation is at least 50° C.

10. The process of claim 8, wherein said reaction temperature is in the range of from 70° and 200° C.

11. The process of claim 1, wherein said molecular ratio of carbon monoxide to oxygen for the oxidative carbonylation is at least 4:1.

12. The process of claim 4, wherein said metal halide is sodium iodide.

13. The process of claim 1, wherein dimethyl oxalate is produced at a space/time yield of >96 g/l/hour.

14. The process of claim 1, comprising using a $C_1$-$C_2$ alkyl derivative of ammonia.

15. The process of claim 14, comprising using a methyl derivative of ammonia.

16. The process of claim 1, comprising using a $C_1$-$C_2$ alkyl derivative of hydrazine.

17. The process of claim 16, comprising using a methyl derivative of hydrazine.

18. The process of claim 1, comprising using dicyanogen or an alkyl nitrile.

19. The process of claim 18, comprising using a $C_1$-$C_2$ alkyl nitrile.

20. The process of claim 19, comprising using a methyl nitrile.

21. The process of claim 1, comprising using acrylic nitrile or methacrylic nitrile.

22. The process of claim 1, comprising using N-($C_1$-$C_2$) alkyl derivative of an amide or hydrazide of a $C_1$-$C_2$ carbonic acid.

23. The process of claim 22, comprising using a N-methyl derivative of an amide of hydrazide of an $C_1$-$C_2$ carbonic acid.

* * * * *